United States Patent [19]
Kronenthal et al.

[11] Patent Number: 5,755,706
[45] Date of Patent: May 26, 1998

[54] FLEXIBLE STRANDED SPONGE PACK

[75] Inventors: Richard L Kronenthal, Fair Lawn; Arthur A. Gertzman, Bridgewater, both of N.J.; Douglas R. Valentine, Oakdale, Conn.

[73] Assignee: Xomed Surgical Products, Inc., Jacksonville, Fla.

[21] Appl. No.: 121,525

[22] Filed: Sep. 16, 1993

[51] Int. Cl.⁶ .............................. A61F 13/15; A61M 29/00
[52] U.S. Cl. .......................... 604/358; 604/904; 606/196
[58] Field of Search .............................. 604/1, 11, 12, 604/286, 358, 904; 606/196, 199

[56] References Cited

U.S. PATENT DOCUMENTS

| | | |
|---|---|---|
| 1,326,616 | 12/1919 | Schuler . |
| 1,381,829 | 6/1921 | Hartman . |
| 2,972,350 | 2/1961 | Deker . |
| 3,797,496 | 3/1974 | Loiacono . |
| 3,911,922 | 10/1975 | Kliger . |
| 3,965,905 | 6/1976 | Schoenholz et al. .............. 604/904 |
| 4,020,844 | 5/1977 | Vickery . |
| 4,098,720 | 7/1978 | Hwa . |
| 4,457,756 | 7/1984 | Kern et al. .............. 604/286 |
| 4,950,280 | 8/1990 | Brennan .............. 606/196 |

*Primary Examiner*—Mark O. Polutta

[57] ABSTRACT

A surgical sponge device comprising a porous cellular absorbent sponge which is cut into rigid segments. The segments are slidably mounted on a strand with a stop to keep the segments from falling off of said strand. The strung segments may be covered by a fluid impervious sleeve which, when removed, allows the rigid segments to wick up fluid to expand from a compressed condition to a predetermined larger size.

26 Claims, 3 Drawing Sheets

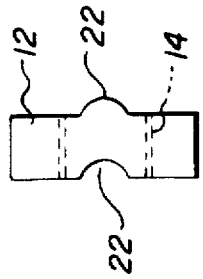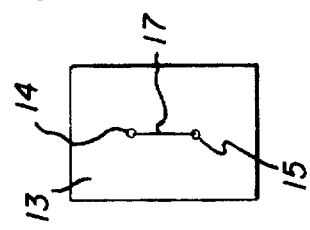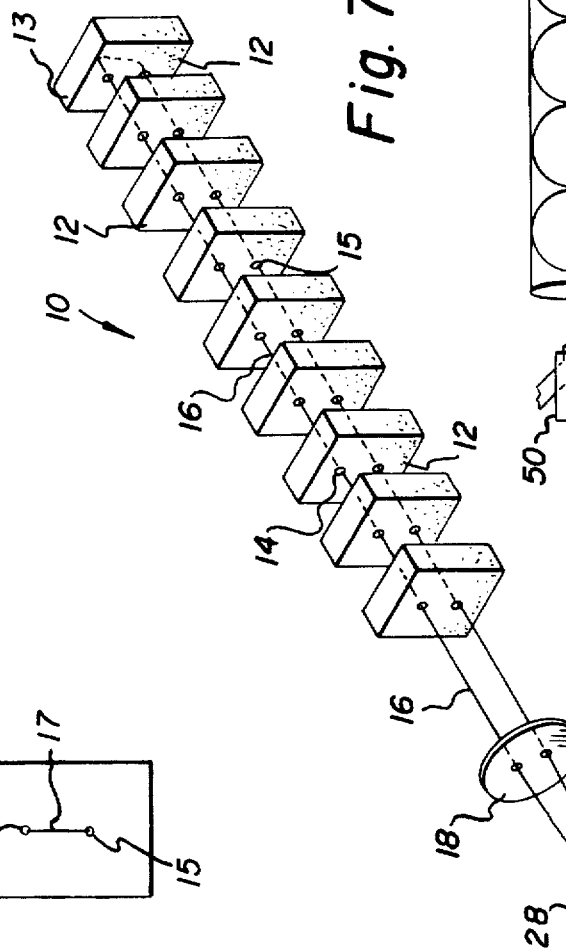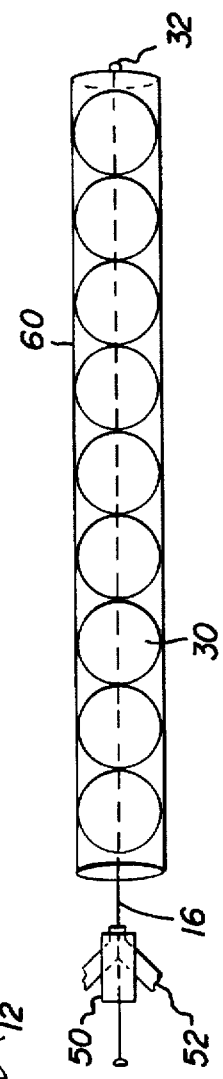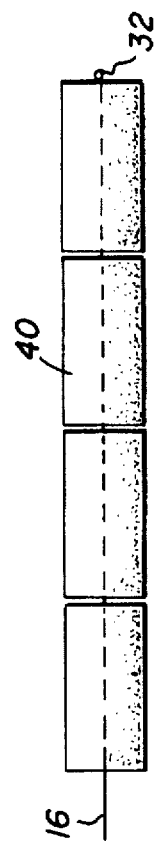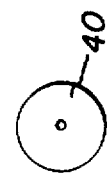

FLEXIBLE STRANDED SPONGE PACK

BACKGROUND OF THE INVENTION

The present invention generally relates to a surgical sponge device and more directly relates to a sterile, multi-member, strung tissue cavity pack which absorbs fluids such as blood, mucous secretions and other materials during the period the pack is in place. Absorption of these fluids into the packing also prevents them from draining into patient organs and causing complications. A typical example for the use of such a pack is in nasal surgery.

There are a number of packs being commonly used during nasal surgery. It is to be understood that nasal surgery is a general term referring to nasal, sinus, transphenoidal, or other procedures whose access is gained through the nasal cavity. Commonly absorptive gauze packs are used for such surgery.

Gauze packs have many disadvantages and are known to cause damage to the nasal lining during insertion and removal. The lint from the pack may pick-up bacteria from non-sterile areas of the operating room and then serve as a carrier of bacteria into the exposed body cavity of the operative patient or create undesirable foreign body reactions such as granulomata or adhesions. Since gauze packs are used to sponge and pack organs and tissues during surgery, intimate tissue contact can cause serious trauma because of the pack's abrasiveness. As the gauze packs absorb blood and other body fluids, they become progressively less pliable and stiffer, thus tending to continue the undesirable abrasive effect.

There have been many uses of sponge type devices in the medical art. U.S. Pat. No. 3,797,496 is directed to a post extraction pad for dentistry. Through a succession of pressing and cutting operations, individual spherical pads are formed with a planar circumferential rim joined to an adjacent circumferential rim for insertion into an area of tooth extraction.

U.S. Pat. No. 3,911,922 discloses a surgical sponge with a porous fabric coated on both sides with an aqueous, liquid-absorbing, flexible foamed polymer with a loop handle stitched to one side of the sponge through the foam layers.

U.S. Pat. No. 4,020,844 discloses the use of a throat pack for use in general anaesthesia comprising a resilient molding of polymeric foam material having a triangular and semi-conical shape adapted for insertion into and occlusion of the oro-pharynx or laryngo-pharynx. The purpose of the throat pack is to resist backward displacement of the tongue. The throat pack is preferably provided with a very thin outer, moisture-impermeable layer, at least on its posterior surface, by applying a coating of polyurethane. An exposed region of the foamed material is used to absorb fluids and one or more safety tapes are incorporated in the throat pack so as to extend outwards through the mouth.

U.S. Pat. No. 2,972,350 discloses a surgical sponge comprising a roll of absorbent material bent into the form of a "U" having its ends secured together. The material may be synthetic cellular sponge material or cotton rolls and the sponge is constructed with a thread or strip of X-ray opaque material passed through the roll.

The Merocel Corporation has used a number of surgical sponges made of the MEROCEL polyvinyl acetal material for post operative applications and such sponges are shown as prior art and are illustrated by the drawings of FIGS. 1-6.

SUMMARY OF THE INVENTION

A multi-sectional surgical sponge assembly comprising a porous, expandable, cellular absorbent sponge material formed of a plurality of individual segments, each of which is slidably mounted on a flexible strand and pre-packaged. The sponge assembly provides individually sectioned rigid members which retain their compressed small volume condition and are contained in a sleeve for insertion into a patient's nasal cavity. The individual member components can be loosened in relation to other member components mounted on the strand to provide overall flexibility allowing the device to be inserted around curves and protuberances within the cavity.

The individual member components wick up fluid from the body to expand from the initial compressed condition to a predetermined larger size to form a shaped surgical sponge assembly and maintain orientation. The surgical sponge assembly is provided with an attaching strand having a length such that one end, remote from the sponge members, is located outside of the nasal cavity and optionally secured to the patient via tape or other means.

An object of the invention is to provide a longitudinally flexible device containing rigid individual absorbent components which is easily insertable, will rapidly absorb up to about 25 times its dry weight in fluids and which can be removed some later time.

Another object of the invention is to provide sponge traction on a strand to resist movement or rotation of one sponge segment relative to another.

In the accompanying drawings, there is shown an illustrative embodiment of the invention from which these and other of objectives, novel features and advantages will be readily apparent.

BRIEF DESCRIPTION OF THE DRAWINGS

FIG. 7 is a perspective view of the present surgical sponge pack invention with individual segmented members spaced from each other;

FIG. 8 is an enlarged front elevational view of the inventive assembly shown in FIG. 7;

FIG. 9 is an enlarged side elevational view of a modified individual member of the surgical sponge pack having a locking recess and protuberance;

FIG. 10 is a side elevational view of the inventive nasal sponge assembly using individual spherical segments inside a sleeve;

FIG. 11 is a side elevational view of the inventive nasal sponge assembly using individual cylindrical segments;

FIG. 12 is an enlarged front elevational view of the inventive assembly shown in FIG. 11.

DETAILED DESCRIPTION OF THE EMBODIMENT

Figure 1:
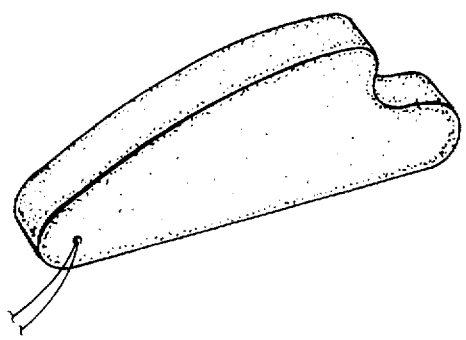
FIG. 1 is an expanded prior art nasal pack device.
Figure 2:
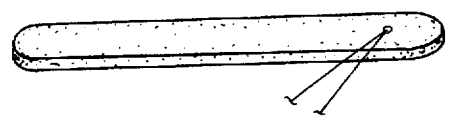
FIG. 2 is the compressed form of the device of FIG. 1.
Figure 3:
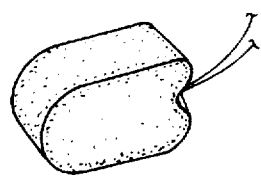
FIG. 3 is an expanded prior art sinus-pak device.
Figure 4:
FIG. 4 is the compressed form of the device of FIG. 3.
Figure 5:
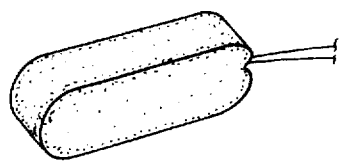
FIG. 5 is a prior art expanded nasal pack device.
Figure 6:
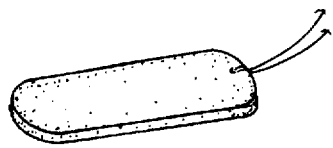
FIG. 6 is the compressed form of the device of FIG. 5.

A preferred embodiment and best mode of the invention is shown in FIGS. 7 and 8. In the invention, a sterile surgical sponge 10 for use in a patient undergoing nasal or sinus surgery or the like is constructed of a plurality of individual members 12 slidably mounted on a surgical strand 16. Each member 12 is constructed of compressed polyvinyl acetal material having a controlled pore size uniformly distributed throughout its volume which is fast wicking and has a high liquid holding capacity. The sponge material has an instantaneous absorbency time and expands uniformly to absorb water to the extent of up to 25 times the sponge weight and has a retained holding capacity of 16 times its own weight in fluid as measured by ASTM D 1117-80. The material is marketed under the trademark MEROCEL by the Merocel Corporation and the material is specifically described by U.S. Pat. No. 4,098,720 issued Jul. 4, 1978 entitled Medical Surgical Sponge and Method of Making Same.

A sterile surgical sponge is manufactured by die cutting or slicing and compressing the sponge material. The rigid, compressed sponge body is cut into segments which may be bored and threaded on a strand and placed in adjacent, selective, engaging relationships with each other. Alternatively, the rigid body may be bored prior to cutting into individual segment members.

The surgical sponge device 10 was segmented into rectangular discs by slicing a rectangularly shaped base body into rectangular disc members 12, each disc 12 being approximately 0.6 cm wide. A total of twelve discs were prepared making a total length of the device about 7.0 cm. Two holes, 14 and 15, with diameters of 1/64 of an inch were drilled into each disc segment member 12. It is noted that any number of members having varying size thickness can be used as long as they will not preclude flexibility of the device. A size "O" monofilament nylon suture 16 was threaded through one hole 14 looped 17 around the end member 13 as seen in FIG. 8 and re-strung back through the other hole 15 in each member creating a "strand of beads" configuration.

The sponge segments 12 can be alternatively stabilized by using two separate monofilaments or strands 16 through the separate holes 14 and 15 in each segment member. The strand(s) 16 can also take the form of a braided or other multimember strand which will increase the friction compared to monofilaments. The strand can also have a flat geometry and be corrugated to increase friction and utility. When a strand of any construction is used, a knot is placed on each end of the strand(s) taking the place of the loop 17 which acts as a fail-safe if a strand is broken. A slide button 18 is slidably mounted on the strand 16 and a double square knot 28 is tied approximately three inches from the proximal end of the first segmented rectangle to prevent the member segment 12 and slide button 18 from sliding off the strand 16.

The member segments 12 can be slid by the user's fingers or by slide 18 against the end member segment 13 which is held in a fixed position by loop 17 or if only one string or strand is used, as seen in FIGS. 10 and 11, against distal knot 32, thereby stiffening the assembly of members 12 into an essentially rigid but conformable device. As long as the tension is maintained by pushing slide 18 against the member segments causing then forcibly to abut against each other and against the loop knot 17 or knot 32, the pack will have maximum stiffness, essentially equal to an unsegmented pack of the same cross sectional dimension. Should a user encounter an obstruction as the pack is inserted, the tension of the member segment 13 against the loop 17 or the knot 32 can be reduced thereby allowing the member segments 12 to shift along the fiber axis of the strand and greatly increase the flexibility of the assembly. The flexibility can be adjusted from stiff to flexible as many times as needed during insertion.

If desired, stability can be further improved as seen in FIG. 9 by forming each segment 12 with a notch or seat 20 on one side and protuberance 22 on the other side which serve to stabilize the segments into a contiguous configuration enabling the geometric cross sections of the members to be aligned along the entire length of the device. In addition to the rectangular shaped segments shown in FIG. 1, spherical shaped segments 30 as seen in FIG. 10 or cylindrical shaped segments 40 as seen in FIG. 11 can be used. Other configurations such as oval and triangular are envisioned.

Figure 13:
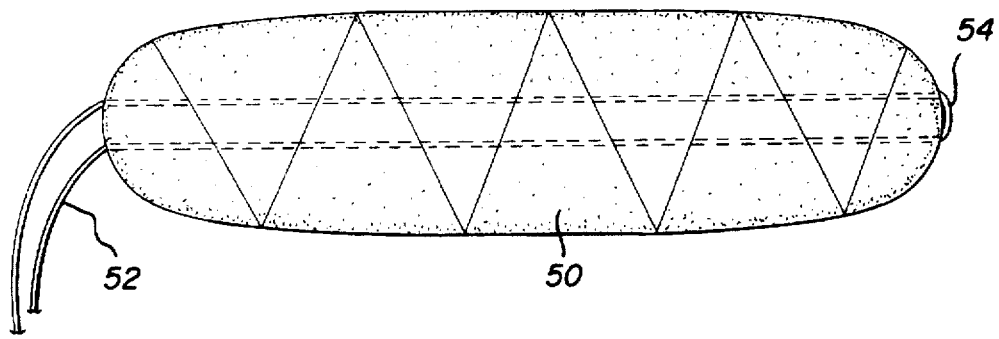
FIG. 13 is a side elevational view of a compressed and segmented triangular embodiment of the invention.
Figure 14:
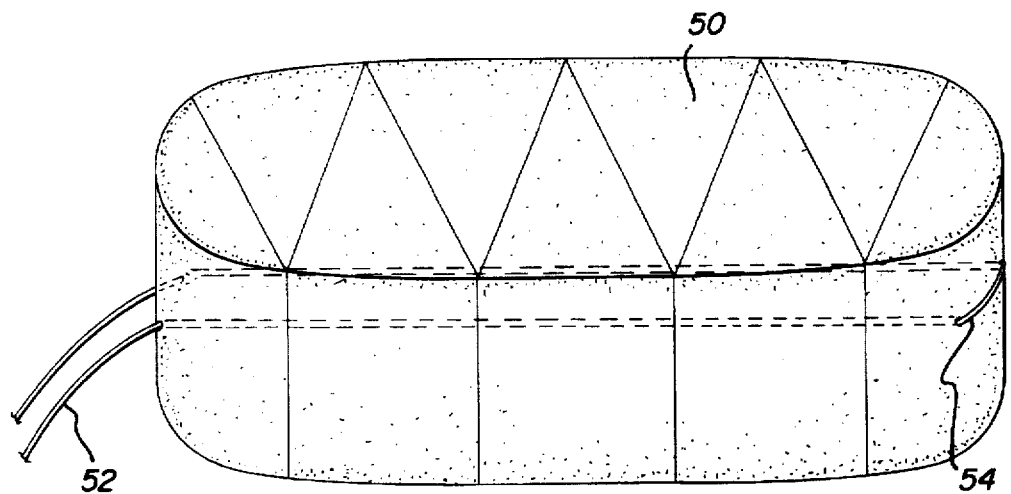
FIG. 14 is a perspective view of the hydrated triangular embodiment shown in FIG. 13.

A triangular embodiment is shown in FIGS. 13 and 14. FIG. 13 shows a cross sectional view of compressed and segmented triangles 50 with a suture 52 and suture loop 54 inserted through the segments. It is recognized that the triangular segments can be cut to form other dimensional shapes such as the oval shape shown in FIG. 14 which is the expanded form of FIG. 13. The triangular segments 50 introduce flexibility for product insertion into a body cavity while resisting movement of one segment relative to another.

The nasal packing is provided with a filament, thread or strand 16 threaded through each sponge member segment 30. This strand can be in the form of a flat or round monofilament, braid, multifilament or extruded flexible rod. It will be appreciated that the filament, thread or strand 16 may also be used for withdrawal of the sponge assembly after use. The proximal end of the thread is provided with a knot 32 which allows the thread to be easily pulled. Alternatively, the proximal end of the thread can fastened to a button 18 as shown in FIG. 7 to allow for easy removal of the device. The button 18 acts in the dual capacity of a slide and handle.

In this and other discussed embodiments, the flexible, stranded nasal sponge can have the component sponge segments mounted such that friction between sponge segments and the through-strand aids the prevention of one segment rotating relative to another. The segments can be strung with a sewing needle, preferably a taper point needle or other non-cutting needle. Alternatively, a small hypodermic tube (approximately 22 gauge) can be passed through a dry, expanded (nonsegmented) sponge body. The strand is passed through the hypodermic tube with a sewing needle or other leader. The nasal sponge is then cut into segments with the tubing preventing the strand from being severed. Removal of the hypodermic tubing and knotting the end of the strand are then completed.

Manufacturing by either of the above two methods or a similar procedure produces a flexible, strung nasal sponge with segments that resist rotation and movement relative to one another. Placement of the strand through the nasal pack in the expanded orientation followed by mechanical compression of the product results in greater friction between the dry compressed sponge segments and the strand. Ease of insertion into the nasal passage is also provided due to its decreased size.

The friction between the sponge segments and strand(s) results from "sewing" compared to drilling or boring passages of a diameter larger than the strand as detailed previously.

In the embodiment of FIG. 10, cinch clip 50 is employed to slide the member segments 30 against the distal restriction (monofilament knot[s] or end loop). The cinch clip 50 is designed to be releasable for easing the tension normally maintained against the knot 32; reduced tension allows passage of the pack past obstructions. The cinch clip 50 is also re-settable to re-establish tension of the sponge segments against the knot and reestablish the desired stiffness.

The cinch clip 50 can optionally include an automatic tensioning spring assembly 52 whereby the monofilament(s) 16 passed through the member 30 and the spring assembly 52 will be automatically tensioned against the distal knot 32 when the clip is in position one. The second position of the clip would allow the monofilament and the segmented members to be relaxed and become flexible. The cinch clip could also be made to provide infinite adjustability between the two positions described above.

A further addition to the use of the sponge assembly regarding controlled hydration and subsequent expansion of the supplied (compressed and dry) sponge uses an outer flexible sheath or sleeve 60. The wicking rate of fluid into the compressed sponge packing and consequent expansion is very fast. This expansion limits and impedes both the insertion of the packing into the body cavity as well as repositioning it to achieve proper placement. Use of an outer flexible sheath or sleeve 60 over the dry, compressed sponge member will allow the following advantages.

1. The clinician can control the time of the pack expansion by removing the sheath at the desired time (after insertion).
2. The sheath can be composed of a material that is both liquid impermeable to prevent premature hydration/expansion and lubricious to ease insertion into the nasal vestibule. Possible sheath materials include polyvinyl chloride, polyolefins, silicone rubber and polytetrafluroethylene, etc. Lubricants can be selected from K-Y jelly, Vaseline, etc.
3. The sheath can be injection molded with a luer or other appropriate fitting to allow insertion of medicament-containing creams or ointments (onto the sponge exterior) after sponge placement. Alternatively, the product may be prepackaged with cream within the sheath.
4. The sheath is formed around the flexible, member segments so as to prevent rotation of one member segment relative to another while allowing small rotations and other directional movements to afford the desired flexibility. The sheath could be molded to match the dimensions of the cavity as, for example, the nasal area. Alternatively, the sheath could be comprised of a heat-shrink polymer (polyolefins, for example) which is exposed to heat after placement over the segmented nasal. A low temperature heat shrink sleeve such as polypropylene could be used, for example. The sheath can be crimped or corrugated in the circumferential direction to provide additional flexibility.

The surgical sponge can, of course, be available in several sizes and shapes to accommodate various size cavities as well as cavities other than the nasal orifice, e.g., the rectum or the ear.

In one example of an operation, the surgical sponge is inserted into the patient's nasal cavity. Because of the initial compressed condition of the sponge, it can easily be inserted into position. As previously noted, it is then hydrated causing the sponge material to expand within the cavity. Removal of the sponge is easily accomplished by tensioning the strand 16 or button 18 and pulling the sponge assembly 10 out of the cavity.

In the foregoing description, the invention has been described with reference to a particular preferred embodiment, although it is to be understood that specific details shown are merely illustrative, and the invention may be carried out in other ways without departing from the true spirit and scope of the following claims:

What we claim is:

1. A surgical sponge assembly comprising a plurality of absorbent, compressed sponge members slidably mounted on a flexible strand means, each of said compressed sponge member being adapted to be moved along said strand means to obtain engagement with adjacent sponge member surfaces, a retaining means providing a stop for the last sponge member located at the distal end of said flexible strand means, said sponge assembly when its sponge members are in engagement allowing direct placement of the sponge assembly in a cavity of a patient and when coming in contact with fluid, swelling to move along said strand means and form an enlarged flexible cross sectional configuration which substantially fills at least a portion of the cavity.

2. A surgical sponge assembly as claimed in claim 1 wherein said each sponge member has a rectangular cross section.

3. A surgical sponge assembly as claimed in claim 1 wherein said each sponge member has a spherical cross section.

4. A surgical sponge assembly as claimed in claim 1 wherein said each sponge member has a cylindrical cross section.

5. A surgical sponge assembly as claimed in claim 1 wherein said each sponge member has a oval cross section.

6. A surgical sponge assembly as claimed in claim 1 wherein said each sponge member has at least one triangular shaped face.

7. A surgical sponge assembly as claimed in claim 1 wherein said each sponge member has a triangular cross section.

8. A surgical sponge assembly as claimed in claim 1 wherein said retaining means comprises a loop.

9. A surgical sponge assembly as claimed in claim 1 wherein said retaining means is a knot at an end of said flexible strand.

10. A surgical sponge assembly as claimed in claim 1 where said flexible strand means is a monofilament.

11. A surgical sponge assembly as claimed in claim 1 where said flexible strand means is a multifilament.

12. A surgical sponge assembly as claimed in claim 1 where said flexible strand means is a braided strand.

13. A surgical sponge assembly as claimed in claim 1 where said flexible strand means is an extruded rod.

14. A surgical sponge assembly as claimed in claim 1 wherein said flexible strand means is a plurality of strands.

15. A surgical sponge assembly as claimed in claim 1 wherein said flexible strand means is a flat strand.

16. A surgical sponge assembly as claimed in claim 1 wherein said flexible strand means is a corrugated strand.

17. A surgical sponge assembly as claimed in claim 1 wherein said flexible strand means is a ribbon strand.

18. A surgical sponge assembly as claimed in claim 1 wherein said flexible strand means has a slide mounted on one end.

19. A surgical sponge assembly as claimed in claim 1 wherein said flexible strand has a slide with a spring tensioning cinch clip mounted on one end.

20. A surgical sponge assembly as claimed in claim 1 wherein each of said sponge members has a body which defines a recess and protuberance which are respectively adapted to mate with a corresponding recess or protuberance of an adjacent sponge member.

21. A surgical sponge assembly as claimed in claim 1 wherein a plurality of said sponge members have a body which defines a recess and protuberance which are respectively adapted to mate with a corresponding recess or protuberance of an adjacent sponge member.

22. A surgical nasal pack comprising a plurality of absorbent sterile sponge body members with fast wicking capability allowing immediate absorbtion of body fluids slidably mounted on a flexible strand means, a stop provided on the distal end of said strand means, a slide moveably mounted on the proximal end of said strand means, said slide being adapted to be moved along said strand means toward the distal end of said strand means to engage one of said sponge body members and drive the sponge body members together so that each sponge body engages the adjacent sponge body member forming a rigid nasal pack allowing insertion of the nasal pack into a nasal cavity, said slide being adapted to be moved away from the distal end to allow sponge body members to move apart in relation to each other providing flexibility of the nasal pack, the nasal pack when placed in a patient cavity and contacting fluid, expanding to occupy said patient cavity placing gentle pressure on the patient and absorbing body fluids.

23. A surgical sponge assembly as claimed in claim 22 wherein each sponge member has a rectangular cross section.

24. A surgical sponge assembly as claimed in claim 22 wherein each sponge member has a spherical cross section.

25. A surgical sponge assembly as claimed in claim 22 wherein each sponge member has a cylindrical cross section.

26. A surgical sponge assembly comprising a plurality of absorbent, compressed sponge members slidably mounted on a flexible unitary strand means which extends through said sponge members, a slide member slidably mounted on said flexible strand means, each of said compressed sponge members being adapted to be moved along said unitary strand means by the slide member for selective engagement with adjacent sponge member surfaces, a distal end of said flexible strand means providing a retaining means acting as a stop for the last sponge member positioned at the distal end of said flexible strand means, said sponge assembly when its sponge members are in engagement allowing direct placement of the sponge assembly in a cavity of a patient and when coming in contact with fluid, swelling to move along said unitary strand means and form an enlarged flexible cross sectional configuration which substantially fills at least a portion of said cavity.

* * * * *